US011676701B2

(12) United States Patent
Carter et al.

(10) Patent No.: US 11,676,701 B2
(45) Date of Patent: *Jun. 13, 2023

(54) SYSTEMS AND METHODS FOR AUTOMATED MEDICAL IMAGE ANALYSIS

(71) Applicant: Pearl Inc., West Hollywood, CA (US)

(72) Inventors: Cambron Neil Carter, Los Angeles, CA (US); Nandakishore Puttashamachar, Los Angeles, CA (US); Rohit Sanjay Annigeri, Los Angeles, CA (US); Joshua Alexander Tabak, Los Angeles, CA (US); Nishita Kailashnath Sant, Los Angeles, CA (US); Ophir Tanz, Los Angeles, CA (US); Adam Michael Wilbert, Los Angeles, CA (US); Mustafa Alammar, Los Angeles, CA (US)

(73) Assignee: Pearl Inc., West Hollywood, CA (US)

( * ) Notice: Subject to any disclaimer, the term of this patent is extended or adjusted under 35 U.S.C. 154(b) by 640 days.

This patent is subject to a terminal disclaimer.

(21) Appl. No.: 16/562,286

(22) Filed: Sep. 5, 2019

(65) Prior Publication Data

US 2021/0074425 A1    Mar. 11, 2021

(51) Int. Cl.
*G06T 7/00* (2017.01)
*G16H 30/40* (2018.01)
(Continued)

(52) U.S. Cl.
CPC ........... *G16H 30/40* (2018.01); *G06F 18/217* (2023.01); *G06F 18/2431* (2023.01);
(Continued)

(58) Field of Classification Search
CPC ....... G16H 50/20; G06K 9/6262; G06K 9/628
See application file for complete search history.

(56) References Cited

U.S. PATENT DOCUMENTS

| 5,579,393 A | 11/1996 | Conner et al. |
| 5,839,438 A | 11/1998 | Grattinger et al. |

(Continued)

FOREIGN PATENT DOCUMENTS

| CA | 2275574 C | 7/2003 |
| CN | 107 871 285 | 4/2018 |

(Continued)

OTHER PUBLICATIONS

Ahmed, Musheer, "Augmenting Accountability, Security and Fraud Detection in Health Data Sharing Systems", Georgia Institute of Technology, May 2016.

(Continued)

*Primary Examiner* — Reginald R Reyes
(74) *Attorney, Agent, or Firm* — Knobbe, Martens, Olson & Bear, LLP

(57) ABSTRACT

Systems and methods are provided for automatically marking locations within a radiograph of one or more dental pathologies, anatomies, anomalies or other conditions determined by automated image analysis of the radiograph by a number of different machine learning models. Image annotation data may be generated based at least in part on obtained results associated with output of the multiple machine learning models, where the image annotation data indicates at least one location in the radiograph and an associated dental pathology, restoration, anatomy or anomaly detected at the at least one location by at least one of the machine learning models. A number of different pathologies may be identified and their locations marked within a single radiograph image.

20 Claims, 9 Drawing Sheets

(51) Int. Cl.

| | |
|---|---|
| *G16H 50/20* | (2018.01) |
| *G06N 20/00* | (2019.01) |
| *G06T 11/60* | (2006.01) |
| *G06F 18/21* | (2023.01) |
| *G06F 18/2431* | (2023.01) |
| *G06V 10/25* | (2022.01) |
| *G06V 10/764* | (2022.01) |
| *G06V 10/776* | (2022.01) |

(52) U.S. Cl.
CPC .......... *G06N 20/00* (2019.01); *G06T 7/0012* (2013.01); *G06T 11/60* (2013.01); *G06V 10/25* (2022.01); *G06V 10/764* (2022.01); *G06V 10/776* (2022.01); *G16H 50/20* (2018.01); *G06T 2207/20081* (2013.01); *G06T 2207/20084* (2013.01); *G06T 2207/30036* (2013.01); *G06V 2201/03* (2022.01)

(56) References Cited

U.S. PATENT DOCUMENTS

| | | |
|---|---|---|
| 6,409,504 B1 | 6/2002 | Jones et al. |
| 6,736,776 B2 | 5/2004 | Miles |
| 7,269,278 B2 | 9/2007 | Cong et al. |
| 7,421,398 B2 | 9/2008 | Kimmel |
| 7,472,275 B2 | 12/2008 | Arnouse |
| 7,602,965 B2 | 10/2009 | Hong et al. |
| 7,822,621 B1 | 10/2010 | Chappel |
| 8,417,010 B1 | 4/2013 | Colby |
| 8,463,716 B2 | 6/2013 | Montgomery et al. |
| 8,687,859 B2 | 4/2014 | Yan et al. |
| 8,706,517 B2 | 4/2014 | Rowe et al. |
| 8,761,493 B2 | 6/2014 | Chen et al. |
| 8,768,016 B2 | 7/2014 | Pan et al. |
| 8,929,635 B2 | 1/2015 | Chen et al. |
| 9,020,236 B2 | 4/2015 | Wang et al. |
| 9,339,245 B2 | 5/2016 | Colby |
| 9,477,649 B1 | 10/2016 | Davidson et al. |
| 9,839,402 B2 | 12/2017 | Colby |
| 9,886,178 B2 | 2/2018 | Kendall et al. |
| 10,043,073 B2 | 8/2018 | Ross et al. |
| 10,049,457 B2 | 9/2018 | Abraham et al. |
| 10,201,318 B2 | 2/2019 | Tsuji et al. |
| 10,410,363 B2 | 9/2019 | Dekel et al. |
| 10,426,351 B2 | 10/2019 | Abrams et al. |
| 10,722,191 B2 | 7/2020 | Colby |
| 10,818,386 B2 | 10/2020 | Yao et al. |
| 10,869,608 B2 | 12/2020 | Dormer et al. |
| 10,902,940 B2 | 1/2021 | Lyman et al. |
| 10,937,108 B1 | 3/2021 | Tabak et al. |
| 10,984,529 B2 | 4/2021 | Carter et al. |
| 11,055,789 B1 | 7/2021 | Tabak et al. |
| 2003/0182117 A1* | 9/2003 | Monchi .................. G16H 10/60 704/E15.04 |
| 2005/0027172 A1 | 2/2005 | Benavides et al. |
| 2005/0203777 A1 | 9/2005 | Rosenfeld et al. |
| 2006/0147872 A1 | 7/2006 | Andreiko |
| 2006/0173985 A1 | 8/2006 | Moore |
| 2007/0067185 A1 | 3/2007 | Halsted et al. |
| 2007/0217648 A1 | 9/2007 | Muehlbauer |
| 2007/0271226 A1 | 11/2007 | Zhang et al. |
| 2007/0294104 A1 | 12/2007 | Boaz et al. |
| 2009/0076960 A2 | 3/2009 | Hamel et al. |
| 2011/0119088 A1 | 5/2011 | Gunn |
| 2011/0153351 A1 | 6/2011 | Vesper et al. |
| 2011/0176712 A1 | 7/2011 | Hill et al. |
| 2012/0076422 A1 | 3/2012 | Yang et al. |
| 2012/0148986 A1 | 6/2012 | Yan et al. |
| 2012/0230560 A1 | 9/2012 | Spitz et al. |
| 2013/0022251 A1 | 1/2013 | Chen et al. |
| 2013/0185331 A1 | 7/2013 | Conemac |
| 2014/0142984 A1 | 5/2014 | Wright et al. |
| 2014/0149128 A1 | 5/2014 | Getchius |
| 2014/0278529 A1 | 9/2014 | Matos |
| 2014/0314288 A1 | 10/2014 | Roychowdhury et al. |
| 2014/0355880 A1 | 12/2014 | Xuan et al. |
| 2014/0379361 A1 | 12/2014 | Mahadkar et al. |
| 2015/0046181 A1 | 2/2015 | Adjaoute |
| 2015/0237106 A1 | 8/2015 | Golay |
| 2016/0014288 A1 | 1/2016 | Ono |
| 2016/0038092 A1 | 2/2016 | Golay |
| 2016/0081620 A1* | 3/2016 | Narayanan .......... G01C 22/006 600/595 |
| 2016/0196389 A1 | 7/2016 | Moturu et al. |
| 2016/0220200 A1* | 8/2016 | Sandholm .......... A61B 5/7246 |
| 2016/0267226 A1 | 9/2016 | Xu et al. |
| 2017/0053562 A1 | 2/2017 | Bova et al. |
| 2017/0083672 A1 | 3/2017 | Juneau et al. |
| 2017/0161439 A1 | 6/2017 | Raduchel et al. |
| 2018/0122509 A1 | 5/2018 | Christiansson |
| 2018/0174367 A1 | 6/2018 | Marom |
| 2018/0206940 A1 | 7/2018 | Kopelan et al. |
| 2018/0235437 A1 | 8/2018 | Ozerov et al. |
| 2018/0325484 A1 | 11/2018 | Patel |
| 2018/0366225 A1 | 12/2018 | Mansi et al. |
| 2019/0066835 A1 | 2/2019 | Lyman et al. |
| 2019/0110753 A1 | 4/2019 | Zhang et al. |
| 2019/0130566 A1 | 5/2019 | Niemeijmer et al. |
| 2019/0236614 A1 | 8/2019 | Burgin et al. |
| 2019/0313963 A1 | 10/2019 | Hillen |
| 2020/0012884 A1 | 1/2020 | Zhao et al. |
| 2020/0100724 A1 | 4/2020 | Golay |
| 2020/0134823 A1 | 4/2020 | Emoto et al. |
| 2020/0138518 A1 | 5/2020 | Lang |
| 2020/0146646 A1 | 5/2020 | Tuzoff |
| 2020/0305808 A1 | 10/2020 | Ezhov et al. |
| 2020/0381105 A1 | 12/2020 | Bernard et al. |
| 2021/0012426 A1 | 1/2021 | Brooks et al. |
| 2021/0073977 A1 | 3/2021 | Carter et al. |
| 2021/0224919 A1 | 7/2021 | Tabak et al. |
| 2021/0327000 A1 | 10/2021 | Tabak et al. |
| 2021/0383480 A1 | 12/2021 | Tabak et al. |
| 2022/0215928 A1 | 7/2022 | Tabak et al. |

FOREIGN PATENT DOCUMENTS

| | | |
|---|---|---|
| CN | 208172859 | 11/2018 |
| CN | 109658260 A | 4/2019 |
| EP | 3407229 A1 | 11/2018 |
| EP | 3503 038 | 6/2019 |
| JP | 2005050246 A1 | 2/2005 |
| KR | 2005020139 A | 3/2005 |
| WO | WO2003071380 A2 | 8/2003 |
| WO | WO2018022705 A1 | 2/2018 |
| WO | WO 2021046241 | 3/2021 |
| WO | WO 2021146452 | 7/2021 |
| WO | WO 2022150821 | 7/2022 |

OTHER PUBLICATIONS

"8 Rules for E-Signature Security", SIGNiX, 2014.
Reducing Healthcare Fraud in Africa; Genkey Solutions b.v., 2016.
McCormick, John, "AI Helps Spot Dental Fraud", Wall Street Journal, Jan. 24, 2020, available at https://www.wsj.com/articles/ai-helps-spot-dental-fraud-11579861801.
Shankeeth et al., "Automated detection of third molars and mandibular nerve by deep learning" (pp. 1-7), Jun. 21, 2019.
S. B. Kotsiantis, "Supervised Machine Learning: A Review of Classification Techniques", Jul. 16, 2007, Informatica 31 (2007) 249-268.
L. C. Rabelo, A. Jones and Y. Yih, "Development of a real-time learning scheduler using reinforcement learning concepts," 1994.
R. Ho, "Pragmatic Programming Techniques: Characteristics of Machine Learning Model", Feb. 19, 2012, BlogSpot, all pages.
Azmi et al., "Freeman Chain Code Representation in Signature Fraud Detection Based on Nearest Neighbor and ANN Classifiers", 2014.
Calberson et al., "Fraudulent Use of Digital Radiography: Methods to Detect and Protect Digital Radiographs", 2008, JOE, 34(5).
Young-Jun Yu: "Machine Learning for Dental Image Analysis",

(56) References Cited

OTHER PUBLICATIONS

Nov. 29, 2016 (Nov. 29, 2016), XP055430578, Retrieved from the Internet: URL:https://arxiv.org/ftp/arxiv/papers/1611/1611.09958.pdf.

Tian Sukun et al: "Automatic Classification and Segmentation of Teeth on 3D Dental Model Using Hierarchical Deep Learning Networks", IEEE ACCESS, vol. 7, Jul. 15, 2019 (Jul. 15, 2019). pp. 84817-84828, XP011734278, DOI:10.1109/ACCESS.2019.2924262 [retrieved on Jul. 9, 2019].

U.S. Appl. No. 16/562,285, Systems and Methods for Automated Medical Image Annotation, filed Sep. 5, 2019.

Fracaro et al., "The Sensitivity and specificity of Clinical Assessment Compared with Bitewing Radiology for Detection of Occlusal Dentin Caries", American Academy of Pediatric Dentistry 23:3, Mar. 22, 2001,204-210.

Markowitz et al. "In Vitro Study of the Diagnostic Performance of the Spectra Caries Detention Aid", The Journal of Clinical Dentistry, 2015,17-22,vol. XXXVI No. 1.

Lee et al. "Diagnosis and Prediction of Periodontally Compromised Teeth Using a Deep Learning-Based Convolutional Neural Network Algorithm", Journal of Periodontal & Implant Science, Apr. 23, 2018,114-123,Apr 48(2).

Lee et al., "Detection and Diagnosis of Dental Caries Using Deep Learning-Based Convolutional Neural Network Algorithm", Journal of Dentistry, Jul. 25, 2018, 106-111, 77.

Hwang et al. "An Overview of Deep Learning in the Field of Dentistry", Image Science in Dentistry, Mar. 25, 2019, 1-7,49.

Murata et al.,"Towards a Fully Automated Diagnostic System for Orthodontic Treatment in Dentistry," IEEE Computer Society, 2017, 1-8, 13$^{th}$ international conference on eScience.

Aberin et al. "Detecting Periodontal Disease Using Convolutional Neural Networks" Mar. 14, 2019.

Arun Anoop M: 11 Image forgery and its detection: A survey, 2015 International Conference on Innovations in Information, Embedded and Communication Systems (ICIIECS), IEEE, Mar. 19, 2015 (Mar. 19, 2015), pp. 1-9 , XP033192551.

International Search Report and Written Opinion for Application No. PCT/US2020/049237, dated Feb. 8, 2021.

International Search Report and Written Opinion for Application No. PCT/US2021/013475, dated Mar. 15, 2021.

International Search Report and Written Opinion for Application No. PCT/US2022/070051, dated Apr. 21, 2022.

\* cited by examiner

SYSTEMS AND METHODS FOR AUTOMATED MEDICAL IMAGE ANALYSIS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

In the fields of dentistry and other medical disciplines, flawed or inconsistent readings of X-ray images and other medical radiographs are relatively common. For example, in the field of dentistry, an X-ray of a patient's teeth may be examined by a dentist for diagnosis or other purposes using the dentist's own judgment informed by experience and training. An individual dentist, doctor or other health provider may have limited experience with a particular diagnosis, anatomy or anomaly, which may lead to inaccurate or missed diagnoses or treatment recommendations. Furthermore, two health providers may have different opinions with respect to a diagnosis or treatment plan based on review of the same radiograph or set of radiographs captured for a particular patient. In the field of dentistry, dental practices often utilize existing computer software to manage and review captured radiographs as digital image files. Some such existing software or related computer tools further enable a dentist to review the digital files and manually mark (such as via user interface controls) features of interest that the dentist observes in a given radiograph image.

BRIEF DESCRIPTION OF THE DRAWINGS

The foregoing aspects and many of the attendant advantages will become more readily appreciated as the same become better understood by reference to the following detailed description, when taken in conjunction with the accompanying drawings, wherein.

DETAILED DESCRIPTION

Figure 1A:
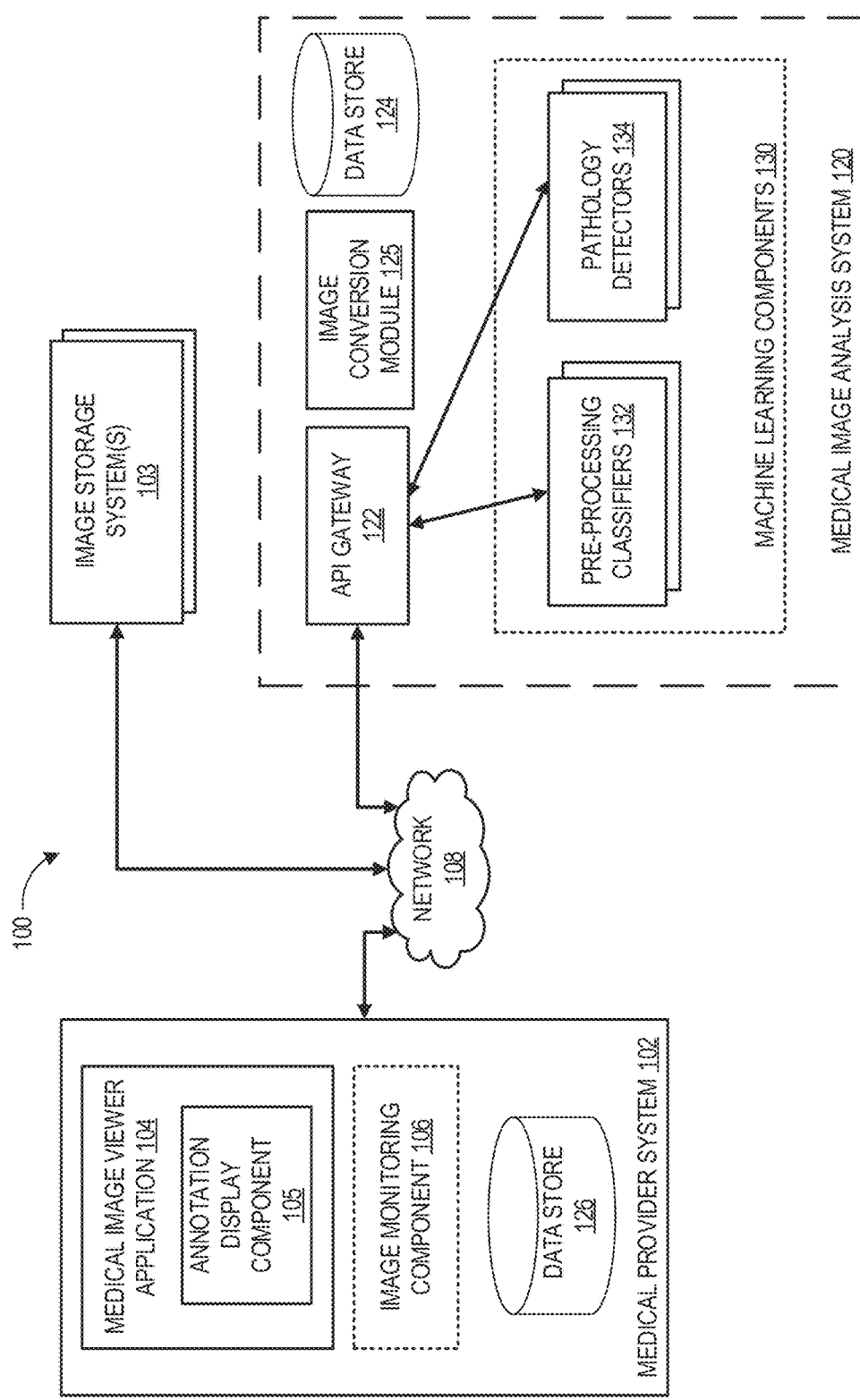
FIG. 1A illustrates a networked computing environment suitable for implementing features of a medical image analysis system and associated client-side medical image viewer application, according to some embodiments.

Generally described, aspects of the present disclosure relate to computer-implemented processes and system architectures for performing automated analysis of dental X-rays and/or other radiographs to label any of a number of different pathologies, anatomies, restorations or anomalies depicted in the captured radiographs. In some embodiments, an application programming interface ("API") is provided that facilitates communications between various components and systems. Functionality implemented via the API may include receiving radiographs as digital files, coordinating associated input and output to a plurality of machine learning models that include models trained to detect specific pathologies, and sending resulting metadata and/or image annotation data to a dentist's or other healthcare provider's computing system. As will be discussed below, in some embodiments, machine learning techniques may be used to train various machine learning models to analyze dental radiographs (such as intraoral dental radiographs taken in bitewing, periapical, panoramic, occlusal and/or other formats) to identify any of a wide variety of different dental pathologies, anatomies, restorations and/or anomalies. The results of providing a particular patient's radiograph data to these trained models may be used by an analysis system to automatically generate annotated images that may be presented to a dentist or other practitioner via a user interface, as will be discussed further herein.

As will be discussed below, an API and associated platform is provided, according to some embodiments, that utilizes computer vision and machine learning functionality to reliably and automatically identify potentially dozens of different pathologies from input radiograph image data. For example, X-ray images, dental cone beam computed tomography (CBCT) images or other radiograph images may be annotated by a number of experts (such as world-renowned dentists) as part of a machine learning model training process, and a collection of trained models may then be used in combination to automatically label or annotate radiographs provided to the trained models in real time or near real time relative to when the images are received via an API. In some embodiments, live feedback from users, such as practicing dentists, may be used to further improve performance of the system in accurately identifying different pathologies.

According to some embodiments, a clinician user can access a patient's radiographs located on an office network server via a medical image viewer application that presents interactive user interfaces on a computing system, such as a laptop or desktop computer connected to a network. The radiograph image or images of the patient's mouth may be captured, sent to a network-based medical image analysis system for analysis and annotation via machine learning, and returned for viewing within the medical image viewer application (such as in ten seconds or less, in one embodiment). Detected conditions or pathologies may be displayed as animated or static overlays that appear over an original X-ray image within a user interface. The overlays may indicate to the practitioner which regions of the X-ray contain which detected conditions or pathologies. As will be discussed below, the clinician can make a number selections within the user interface to alter the display, such as selecting a specific conditions for viewing.

FIG. 1A illustrates a networked computing environment suitable for implementing features of a medical image analysis system and associated client-side medical image viewer application, according to some embodiments. The environment 100 includes a network 108, a medical provider system 102, one or more image storage systems 103, and a medical image analysis system 120. To simplify discussion and not to limit the present disclosure, FIG. 1A illustrates only one medical provider system 102, though multiple medical provider systems may be present in many embodiments. For example, the medical provider system 102 may be utilized by a specific dental practice or dentist, and a number of other dental practices or other healthcare providers may operate other medical provider systems that are in communication with the same medical image analysis system 120. The medical provider system 102 may be operated by a user within a variety of dental settings, such as primary care (for example, family dental practice or internal medicine), emergency medicine, urgent care, and/or oral maxillofacial radiologists who review radiographs across these settings. For example, the medical image viewer application 104 may be installed on one or more computer systems within dental clinics, dental service organization offices, dental insurance providers and/or other settings.

The medical image analysis system 120 can include API gateway 122, one or more data stores 124, an image conversion module 125, and machine learning components 130, which in the illustrated embodiment include multiple preprocessing classifiers 132 and pathology detectors 134. While FIG. 1A specifically illustrates pathology detectors, the machine learning components 130 may additionally include various other detectors that are each trained to detect something other than a pathology, such as various anatomies, anomalies and/or restorations. As will be discussed below, the API gateway 122 can communicate with the medical provider system 102 and/or image storage system 103 (e.g., using a network 108, such as the Internet) to receive medial images, and coordinate subsequent image processing and analysis by the machine learning components 130. Although only one network 108 is illustrated, multiple distinct and/or distributed networks may exist. The various systems and other components illustrated in FIG. 1A, including interactions or communications between them, will be described in more detail below with respect to FIG. 1B.

The medical provider system 102 illustrated in FIG. 1A may include hardware and software components for establishing communications over a communication network 108. For example, the medical provider system 102 may be equipped with networking equipment and network software applications (for example, a web browser and/or a proprietary application associated with an operator of the medical image analysis system 120) that facilitates communications via one or more networks (for example, the Internet, an intranet or a virtual private network). The medical provider system 102 may have varied local computing resources such as central processing units and architectures, memory, mass storage, graphics processing units, communication network availability and bandwidth, and so forth. Further, the medical provider system 102 may include any type of computing system. For example, the medical provider system 102 may include one or more desktop computers, laptop computers, and/or servers operated in association with a dental practice or other medical practice, in some embodiments.

The medical provider system 102 can include a data store 126. The data store 126 can be configured to store patient data, radiograph images, and/or other information used in a typical dental practice or other medical practice. The data store 126 may be local to the medical provider system 102 (such as physically located within a doctor's office, hospital, lab or other medical facility), remote from the medical provider system 102, and/or distributed across multiple computing devices. The data store 126 may employ various security and privacy protocols known in the art for storage of medical data, including Health Insurance Portability and Accountability Act ("HIPAA") compliance. In some embodiments, the data store 126 may be written to by a dental practice's existing third-party practice management and/or radiograph processing application(s), and may be monitored for new files by an image monitoring component 106 that is configured to operate in association with the medical image viewer application 104 and medical image analysis system 120.

The medical provider system 102 may include an image monitoring component 106 configured to monitor the data store 126 or other source of a dental practice's radiograph images for new images, as will be further discussed below. In some embodiments, the image monitoring component 106 may be a stand-alone application or system extension, while in other embodiments it may be part of the medical image viewer application 104. The medical image viewer application 104 may be a computer program or application executed by the medical provider system 102 to provide various client-side functionality that will be described herein, and may include an annotation display component 105 for generating and causing display of annotated radiograph images and associated user interfaces, as will be further described below.

Figure 1B:
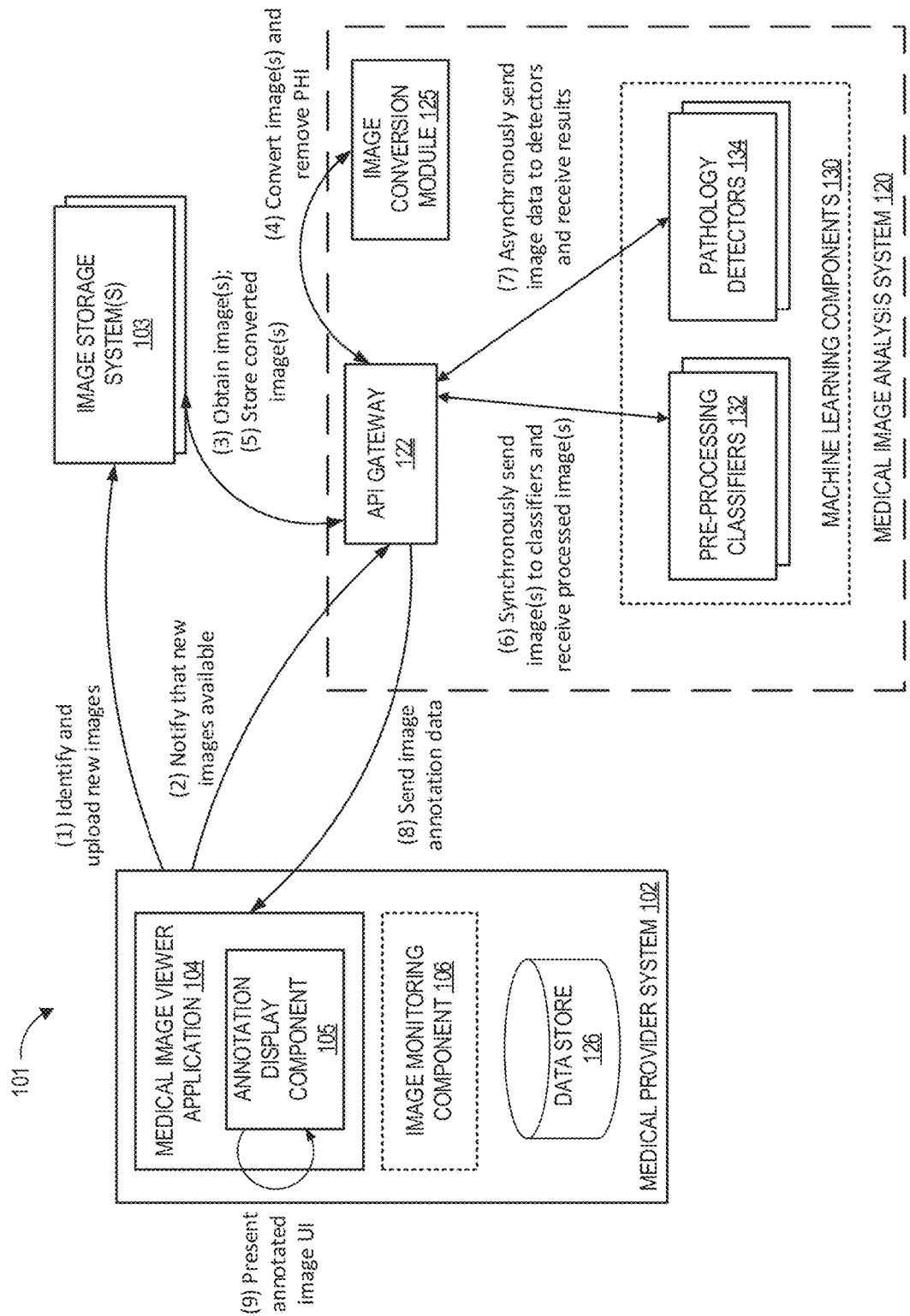
FIG. 1B illustrates example data flow within the networked computing environment of FIG. 1A.

FIG. 1B illustrates example data flow 101 within the networked computing environment of FIG. 1A. For ease of illustration, the data flow of FIG. 1B does not specify whether individual communications between illustrated components or systems are over a network or are local within a single computing system or device. While one example network arrangement is illustrated in FIG. 1A and described above, it will be appreciated that components or subsystems illustrated as part of a single computing system in FIG. 1A may instead be remotely located relative to each other. Similarly, other systems or components illustrated as in network communication with each other in FIG. 1A may in some embodiments be operated together on a single computing system or may be in direct local communication with each other rather than communicating over a network.

The illustrative data flow 101 begins at step (1) with the medical provider system 102 identifying and uploading one or more new radiograph or other medical images to an image storage system 103. In some embodiments, the image monitoring component 106 may be configured to periodically scan or search a specific directory or location on the data store 126 for newly available radiograph image files that have been stored by another application associated with capturing X-rays of patients (not illustrated), such as any of a number of existing X-ray image management applications or software packages utilized by dentists or other medical professionals. For example, the image monitoring component 106 may be configured to check a specific directory for any new image files added to the directory since a previous check performed by the image monitoring component, where such checks may occur on a set schedule, in response to a user request, and/or based on another trigger event (such as a trigger invoked by the medical image viewer application 104).

The images and associated metadata sent to the image storage system 103 at step (1) may be sent in a secure manner. For example, in one embodiment, the images and any associated data may be sent via a Transport Layer Security ("TLS") cryptographic protocol over a Hypertext Transfer Protocol Secure ("HTTPS") connection, and the image storage system 103 or associated cloud storage service may be HIPAA certified. For example, the data stored in image storage system 103 may be stored within a bucket that is fully encrypted and which has tightly controlled access restrictions (such as using two-factor authentication and enforcing HIPAA compliant policies).

At step (2), the image monitoring component 106 may send a notification to the API gateway 122 that one or more new images are available for the API gateway 122 to access from the image storage system 103. In some embodiments, the notification may be sent via an API call. The API call may include an identifier of the particular medical provider system 102 or the associated medical provider, in some embodiments in which the medical image analysis system 120 is configured to provide API functionality across a potentially large number of different medical providers. The notification received by the API gateway may then trigger the API gateway, at step (3) to obtain the one or more newly added images and associated data from the image storage system 103.

Once the medical image analysis system 120 obtains the new image or images via the API gateway 122, the image conversion module 125 may be executed to convert the images and/or remove protected health information ("PHI") or other sensitive data or metadata at step (4). In some embodiments, the images originally stored in the image storage system 103 may have been in a variety of formats depending on the particular file formats and technology employed at a particular medical provider system 102 from which the files originated.

For example, the images may have been originally created by any of a wide range of dental radiograph systems made by different manufacturers and stored on clinical office network servers using digital storage systems offered by any of various third party companies. The original stored image files, for instance, may include files formatted as DICOM, RBG, or JPEG image file formats, among others. In some embodiments, the image conversion module 125 converts all obtained images to a specific format (such as a JPEG) for use with the machine learning components 130 in order to simplify processing and output. At step (5), the converted and/or otherwise modified images may then be stored back in the image storage system 103 (which may include replacing the original files with the converted files) and/or in local storage or another remote data source for use in further analysis by the medical image analysis system 120, as discussed below.

At step (6), the API gateway 122 of the medical image analysis system 120 may begin coordination of machine learning-based analysis of the one or more newly obtained images. For example, the API gateway 122 may first synchronously send the image data to a number of different pre-processing classifiers 132 at step (6), then asynchronously send the image data and/or particular pre-processing results to each of a number of different pathology detectors 134 (and/or anatomy detectors, as further discussed herein). The functionality that occurs at steps (6) and (7) will be further described below with respect to other figures.

Once the API gateway 122 receives the results of the machine learning analysis for one or more particular images, which may be in the form of annotation data, the API gateway at step (8) may send the resulting data to the medical provider system 102. For example, the API gateway may send a responsive API call to the medical image viewer application 104, which may then present the image with annotation data via one or more user interfaces at step (9), such as via the annotation display component 105. In some embodiments, the annotation data sent at step (8) may be pushed to the medical provider system 102 as soon as it is created by the medical image analysis system (such as in real time or near real time), while in other embodiments, the annotation data may be stored by the medical image analysis system 120 and only sent back to the medical provider system 102 in response to a specific request from the medical provider system 102 (which may occur based on an API request initiated by the medical image viewer application 104 when a user requests to view a particular image).

Figure 2:
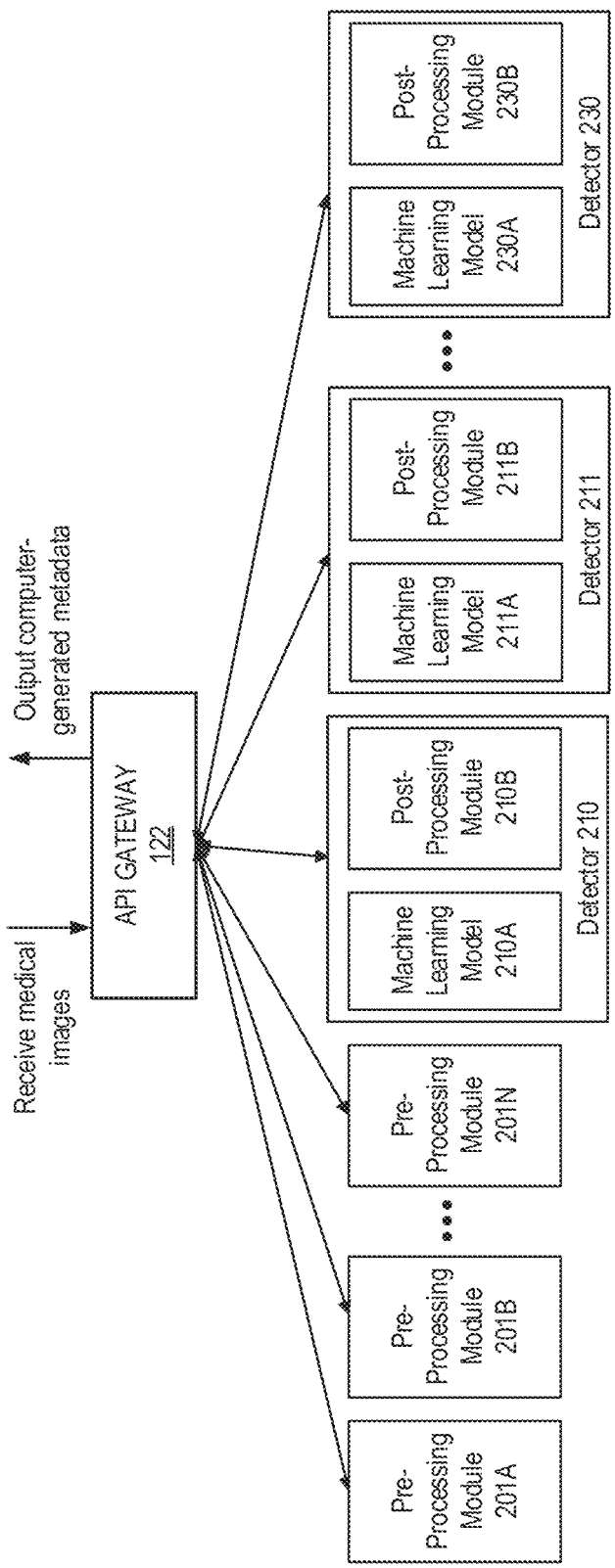
FIG. 2 illustrates a number of different pre-processing modules, machine learning models, and post-processing modules that may be collectively implemented in order to detect different pathologies, anatomies, restorations and/or anomalies depicted in a radiograph.

FIG. 2 illustrates a number of different pre-processing modules, machine learning models, and post-processing modules that may be collectively implemented in order to detect different pathologies, anatomies, restorations and/or anomalies depicted in a radiograph. As discussed above, the API gateway 122 may generally be responsible for managing calls to various routines and models for generating metadata, such as image annotations and associated labels or classifications. As illustrated, the API gateway 122 makes sequential calls to several pre-processing modules which preprocess the image data, which are shown in FIG. 2 as preprocessing modules 201A, 201B through 201N. It will be appreciated that there may be a large number of pre-processing modules not illustrated.

At least some of the pre-processing modules may generally adjust certain global features in X-rays or other radiograph images by way of image processing. These routines may be configured to enhance and/or standardize the image data before it is processed by machine learning models. One such example of pre-processing is histogram equalization. In some embodiments, the pre-processing modules may include, but are not limited to: (a) a module configured to determine if an image is "whitewashed" such that no image processing techniques (e.g. gamma correction) will sufficiently recover useful information for subsequent processing; (b) a module configured to detect the orientation of the image and adjust the orientation such that subsequent models or modules are only required to handle one orientation; (c) a machine learning model configured to detect teeth or another specific anatomical feature; and/or (d) a machine learning model configured to classify the type of image, such as from possible classifications of panoramic, bitewing, periapical, and/or others.

After the pre-processing modules have processed a given image, the API gateway 122 makes parallel calls to a number of different machine learning models (such as machine learning models 210A, 211A, 230A, among others) that have been previously trained to localize and classify (or detect) specific pathologies, anatomies, restorations, and/or anomalies. In doing so, the API gateway may pass forward partial metadata generated from the preprocessing modules, such as preprocessing modules 201A, 201B and 201N. This metadata may then be used by the post-processing routines associated with specific machine learning models, such as post-processing modules 210B, 211B and 230B. As illustrated, each detector 210, 211, 230 and others not illustrated may include both a machine learning model and an associated post-processing module that is specific to the given machine learning model, according to some embodiments.

In some embodiments, each of the specific detectors and/or the associated machine learning model may include one of the following, though others may be implemented or some excluded in other embodiments: a model for detecting the presence of bone loss; a model for detecting the presence of faulty restorations (such as restorations which contain open margins, sub margins, or overhangs); a model for detecting caries; a model for detecting recurrent decay; a model for detecting widened periodontal ligaments; a model for detecting existing restorations (such as crowns, root canals, metal and non-metal fillings, bridges, or implants); a model for detecting potential pathologies (such as cysts, bone lesions, cancerous growths or malignancies); a model to detect calculus; a model to detect existing anatomy (such as sinuses, nerves, nasal canals, orbits, or zygomas); a model to detect teeth by number; a model to detect crowns and roots of teeth; a model to detect the size of the airway; a model to detect quantity and quality of dental implant site; a model to detect third molar impaction; a model to detect jaw fractures; a model to detect facial trauma; a model to detect arch forms of jaws; and/or a model to detect orthodontic cephalometric tracings. In some embodiments, a single model may be trained to identify a large set of the above or all of the above, in addition to individual models that detect individual conditions above.

In some embodiments, both a first model and a second model may each individually be configured to detect multiple pathologies that are the same between the two models, but the models may have been trained using different machine learning algorithms. For example, two models employing different machine learning algorithms may each be trained to classify image data as depicting any of the same list of pathologies (such as twenty different pathologies), but may output different classification results for the same input images based on differences in the respective models' training data and/or specific machine learning algorithm or structure used for the particular model. In such embodiments in which two or more machine learning models may be trained to detect the same or overlapping sets of potential pathologies, the medical image analysis system 120 may be configured to apply a voting methodology or other resolution process to determine an ultimate classification result based on collective output of the models. It will be appreciated that many known methods of ensemble learning may be used in embodiments in which multiple alternative models are trained to make similar classification predictions using different supervised and/or unsupervised machine learning techniques. As discussed above, other models may be specific to individual pathologies (such as a model trained to detect only a single pathology as opposed to any of a set of pathology classes or labels).

As discussed elsewhere herein, training of the various machine learning models may include data collection by way of individual annotation and/or consensus-based annotation. Consensus may be arrived at programmatically in some embodiments, such as based on a Jaccard index being determined to be at or above a given threshold between two individual annotations. Consensus annotation may additionally or alternatively come from annotators directly working together to jointly annotate radiographs together. Once the data has reached an acceptable volume and variance (such as with respect to pre-defined feature spaces) it may be used to train the models and may additionally be used for measuring accuracy of the trained models, as will be further discussed below.

The machine learning architectures used for training may include various forms of neural networks, deep learning models, and/or other architectures for accomplishing classification and/or localization via supervised and/or unsupervised learning. In some embodiments, the specific architectures may be selected to achieve two goals: (1) to localize regions in a radiograph which contain features of interest and (2) to classify each of said regions. The final output in most instances will be some number of predicted regions along with associated probabilities of said regions containing a particular pathology, restoration, anatomy, or anomaly of interest. As non-limiting examples according to some embodiments, one or more of the models may resemble or include single shot detector (SSD), faster region-based convolutional neural networks (Faster R-CNN), "You Only Look Once" (YOLO) real-time object detection, and/or a U-Net convolutional neural network. It will be appreciated that various other existing or future object detection, localization, and/or classification methodologies may be used for individual models, and that different models within a single embodiment may use different training methodologies and/or machine learning architectures.

As shown in FIG. 2, each machine learning model (such as machine learning model 210A) is coupled with a model-specific post-processing module (such as post-processing module 210B). Post-processing modules may merge, edit, and/or augment the produced metadata based on algorithmically combining output from machine learning models. One such example is reducing false positives in anatomical regions in which the predicted property is known never to exist. The functionality implemented by a given post-processing module may vary based on what the associated machine learning model is designed to localize and classify. For example, if machine learning model 211A is configured to classify caries (which can only exist on teeth), the combination of this caries detection model and a tooth detection pre-processing module may be used by the post-processing module 211B to confirm that the machine learning model 211A did not classify a region as caries if the region was not also classified as a tooth in pre-processing.

In some embodiments, certain machine learning models or detectors may produce metadata that is used by a subsequent detector or machine learning model. For example, in one embodiment, detector 211 may be a sub-detector of detector 210. For example, detector 210 may localize a region in the image which has been predicted to contain a specific pathology, anatomy, restoration and/or anomaly. Then, detector 211 may take this metadata as input and restrict its processing to only those regions of interest to it. As a more specific example, detector 210 may predict the presence of caries. Detector 211 may crop only those regions containing caries (as predicted by detector 210), then detector 211 may classify only those regions for the particular type of carie (e.g. into dentin, into enamel, or into pulp). In some embodiments, there may be more than one sub-detector for a given detector. For example, following the example above, there may also be a sub-detector to classify detected carie regions into differing categories, such as gross, mesial, occlusal/incisal, distal, facial, lingual/palatal, incipient, or recurrent. Once all detectors have generated their respective metadata, the API gateway 122 may construct or generate a final output message or metadata set that is passed back as the final response back to a requester.

Figure 3:
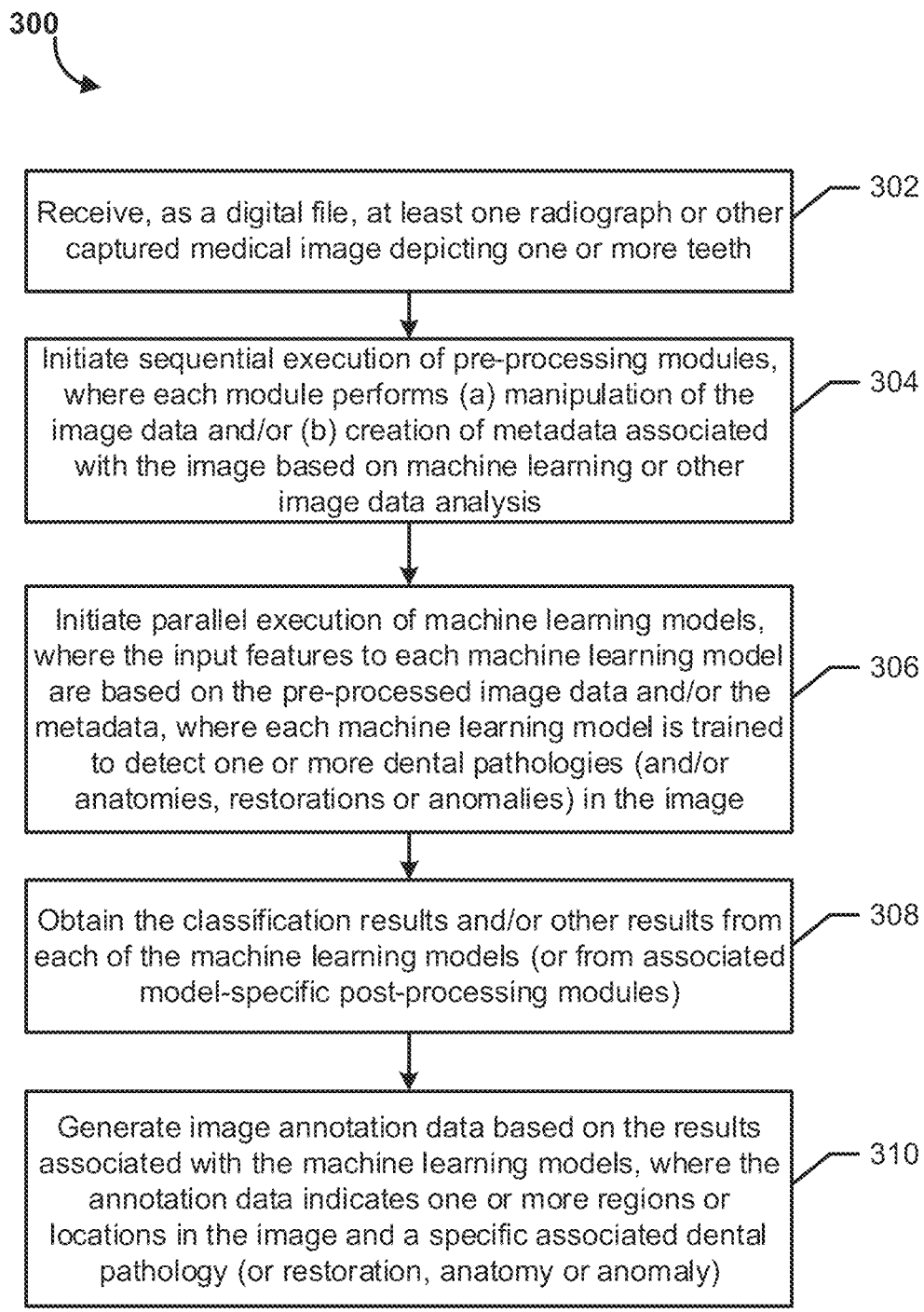
FIG. 3 is a flow diagram of an illustrative method for generating radiograph annotation data based on the output of multiple machine learning models, according to some embodiments.

FIG. 3 is a flow diagram of an illustrative method 300 for generating radiograph annotation data based on the output of multiple machine learning models, according to some embodiments. The illustrative method 300 may be performed by the medical image analysis system 120, in some embodiments. Additional details regarding system functionality implemented at each of the blocks of FIG. 3 are described elsewhere in the present disclosure, and will be generally summarized below with respect to method 300 in a non-limiting manner.

The method 300 begins at block 302, where the medical image analysis system 120 receives, as a digital file, at least one radiograph or other captured medical image, such as an X-ray image depicting a portion of a patient's mouth including one or more teeth. As discussed above, the one or more images may be received by the API gateway 122 as a result of an API call from a computing system associated with a dental practice, such as medical provider system 102. At block 304, the API gateway 122 of the medical image analysis system 120 may initiate sequential execution of two or more pre-processing modules, where each pre-processing module performs one or more of (a) a manipulation of the received image data and/or (b) creation of additional metadata associated with the image based on machine learning or other image data analysis. Pre-processing is discussed both above and further below in more detail.

The results of the pre-processing modules may be passed forward by the API gateway to pathology detectors or other condition detectors at block 306, where the API gateway may initiate parallel execution of a number of different machine learning models (which may each be coupled to a different post-processing module, as will be further discussed herein). The input features to each machine learning model may be based on the pre-processed image data and/or the additional metadata determined at block 304. Each machine learning model may be trained to detect one or more dental pathologies, anatomies, restorations or anomalies present in the image, as further described elsewhere herein. In some embodiments, certain models may be sub-models of another, such that the sub-models receive metadata output of the earlier related model. In some instances, the machine learning models may include ensemble detectors that collectively predict many pathologies, as will be further described below.

The API gateway 122 of the medical image analysis system 120 may obtain the classification results and/or other results from each of the machine learning models or associated model-specific post-processing modules at block 308. Because the pathology detectors 134 may execute in parallel or asynchronously, the API gateway may either wait for all of the results for a given image before generating final annotation data to return to the requesting system (such as medical provider system 102) or may generate and return different portions of the final annotation data iteratively in real time as results are returned from the individual pathology detectors.

The medical image analysis system 120 may generate the image annotation data at block 310 based on the obtained results from the plurality of machine learning models. The annotation data associated with each detected condition may indicate one or more regions or locations in the image and an identifier or label of the specific associated condition (such as a specific dental pathology, restoration, anatomy or anomaly). The annotation data for a given identified pathology or other condition may include, for example, a pathology name label, an x coordinate and y coordinate within the image of a top left point of the bounding region, as well as dimension information defining the bounding region shape (such as a width and height in pixels of a bounding box). The annotation data may additionally include a numeric confidence score regarding the pathology classification, as determined by one or more of the machine learning models. The annotation data may be written to a file or database record that may be stored or sent to a requesting system (such as medical provider system 102), and/or may be returned by the API gateway 122 as parameters or data fields in an API communication with the requesting system. The illustrative method 300 may then end.

Figure 4:
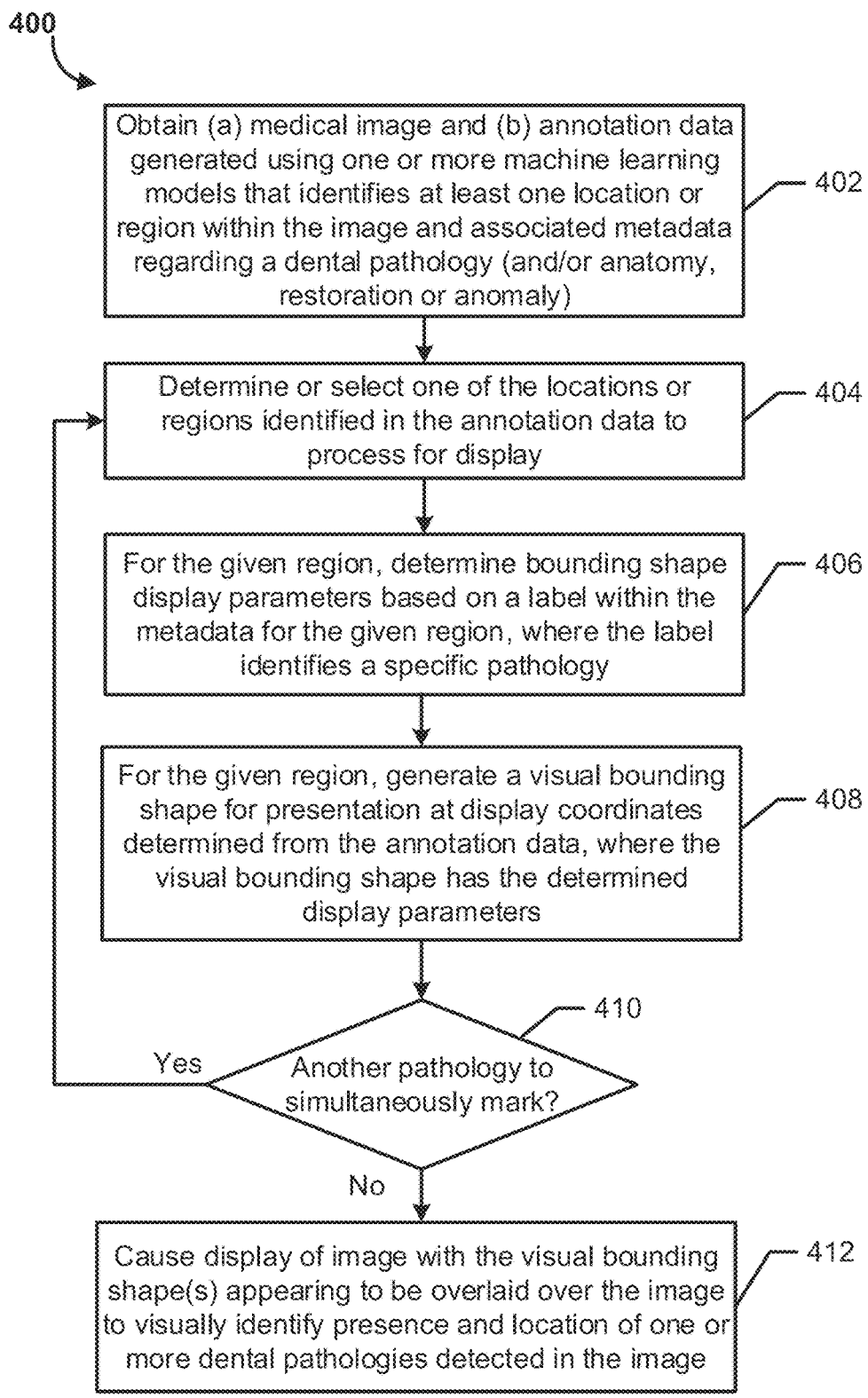
FIG. 4 is a flow diagram of an illustrative method for generating a user interface that includes presentation of radiograph annotation data and/or other metadata automatically determined by machine learning techniques, according to some embodiments.

FIG. 4 is a flow diagram of an illustrative method 400 for generating a user interface that includes presentation of radiograph annotation data and/or other metadata automatically determined by machine learning techniques, according to some embodiments. The illustrative method 400 may be performed by the medical provider system 102 based on interaction with the medical image analysis system 120, in some embodiments. Additional details regarding system functionality implemented at each of the blocks of FIG. 4 are described elsewhere in the present disclosure, and will be generally summarized below with respect to method 400 in a non-limiting manner.

The method 400 begins at block 402, where the medical provider system 102 may obtain (a) a radiograph or other medical image and (b) annotation data generated using one or more machine learning models, where the annotation data identifies at least one location or region within the image and associated metadata regarding a dental pathology, anatomy, restoration or anomaly detected by the machine learning model(s). The metadata may have been generated by the medical image analysis system 120, as discussed above with respect to FIG. 3. In some embodiments, the medical provider system 102 may request the metadata from the API gateway via an API request in response to a user of the medical provider system 102 requesting to view a particular radiograph. In other embodiments, the metadata may have been generated previously by the medical image analysis system 120 (such as on a batch basis) and may be retrieved from local storage at the medical provider system 102 at block 402.

At block 404, the medical provider system 102 may determine or select one of the locations or regions identified in the annotation data to process for display. Block 404 may be the start of a loop implemented by executable code of the medical image viewer application to iteratively process each annotated region in the annotation data for a particular radiograph image. At block 406, for the given image region currently being processed, the medical provider system 102 may determine one or more bounding shape display parameters (such as color, opacity and/or shape type) based at least in part on a label within the metadata for the given region. The label may represent or specify a specific pathology or other classification previously determined by a machine learning model and assigned as a classification label to the given region. In some embodiments, for instance, different pathologies may be assigned different bounding shapes, colors or other display parameters, which may be configurable by a user. In one example, at least one display parameter determined at block 406 may be based on a confidence level determined by one or more models. For example, a specific color and/or opacity may be assigned to the bounding region based on its confidence score, as will be further discussed below.

At block 408, the medical provider system 102 may, for the given region currently being processed, generate for display a visual bounding shape for presentation at display coordinates determined from the region or location data within the annotation data, where the visual bounding shape is generated to have the determined bounding shape display parameters. In some embodiments, this visual bounding shape may be considered an example of overlay content to be presented over the radiograph image. The overlay content may additionally include display of text identifying the label (e.g., identifying the particular pathology name), as will be further discussed with respect to FIG. 5 below.

At decision block 408, the medical provider system 102 may determine whether there are more pathologies to simultaneously mark within the current user interface display. If there is additional annotation data to be processed for display (such as an additional annotation region meeting the confidence thresholds and/or other current filters set within the user interface, as will be described below), the method may return to block 404 to process the next annotation region. Otherwise, at block 412, the medical provider system 102 may cause display of a user interface that presents the image with the visual bounding shape(s) appearing to be overlaid over the image to visually identify the presence and location of one or more dental pathologies, anatomies, restorations or anomalies detected in the image. In some embodiments, pathologies may appear as overlay content in real time as each one is processed. For example, the medical provider system 102 may gradually populate the display of the radiograph with bounding region overlay information as results are received from the various machine learning models. In other embodiments, the system may wait to display overlay content until all regions have been processed for annotated display. The illustrative method 412 then ends.

Figure 5:
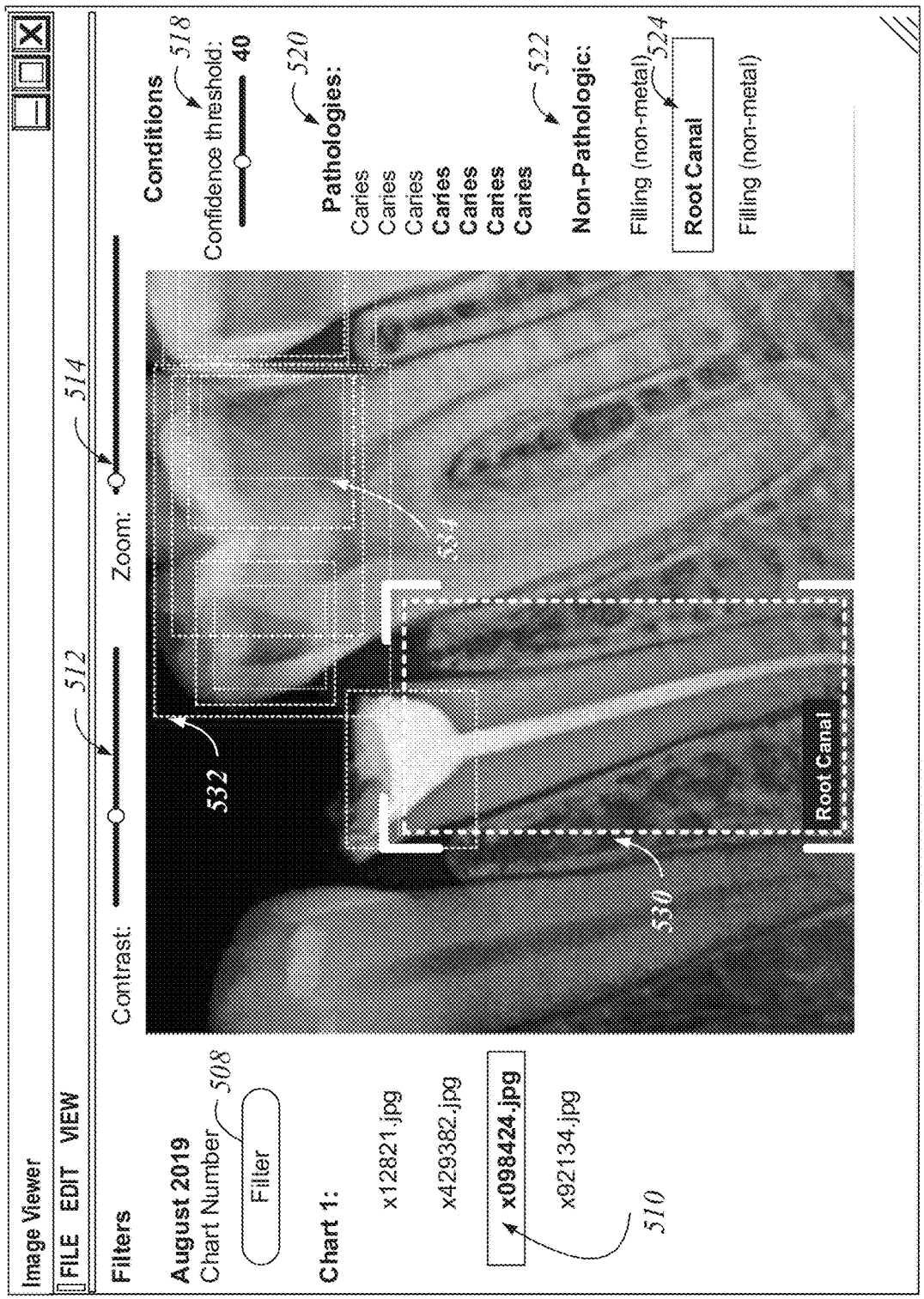
FIG. 5 depicts an illustrative user interface that presents a radiograph that has been annotated based on the results of automated image analysis, along with various user interface controls that enable a viewing user to modify the visual presentation.

FIG. 5 depicts an illustrative user interface 500 that presents a radiograph that has been annotated based on the results of automated image analysis, along with various user interface controls that enable a viewing user to modify the visual presentation. In some embodiments, the user interface may be presented by the medical provider system 102 based on annotation data received from the medical image analysis system 120, such as via API gateway 122. For example, a clinician using medical provider system 102 may have requested to access and view a certain patient's radiographs using the medical image viewer application 104. The medical image viewer application 104 may have requested annotation data from the API gateway in response to the clinician's view request, or may have previously requested the annotation data from the API gateway (in which case the annotation data may be retrieved from a locally stored copy and/or from cloud storage or other remote storage when the clinician requests to view a particular radiograph). As illustrated, detected conditions are displayed as overlay content (such as bounding regions 530, 532 and 534) over an original X-ray image, where each overlay indicates to the practitioner which regions contain which specific detected conditions. The clinician can toggle over the image (such as using a mouse or touchscreen) to select or highlight each specific condition for further review.

The user interface 500 includes filter options that enable the user to filter the available radiograph images by chart number by selecting filter option 508. The imagery and associated metadata may generally be grouped into charts, where a chart pertains to a series of medical images obtained from a single capture event (such as X-rays captured for a given patient in a single session). A list of available images within the currently selected chart (Chart 1) are shown, and the image currently being viewed is indicated by bolded text 510 (reading "x098424.jpg," which may be a filename of the image).

In the illustrated example, pathologies identified in the displayed image (based on the machine learning methods described herein) are listed on the right side of the user interface 500. For example, a number of pathologies 520 are listed and selectable by the user, as well as a number of non-pathologic conditions 522. Bounding region 530 may correspond to the "Root Canal" condition 524 from non-pathologic list 522, while bounding regions 532 and 534 may correspond to specific detected caries from pathologies list 520. Additionally included in the user interface 500 are user interface controls that may be interacted with by the user to modify the display of the image and/or the associated overlay content. These user interface control elements include contrast control 512, zoom control 514 and confidence threshold control 518, each of which will be further described below. While these controls are shown as sliders in the example, in other embodiments other forms of controls may be presented (such as, for example, drop down menus, dedicated zoom in and zoom out buttons, text fields for entering numeric values, and/or others).

In the illustrated example, a clinician may have logged in to a user account associated with the medical image viewer application 104, and then may have entered or selected a customized patent identifier (such as a name or number) of a patient for whom the clinician is interested in viewing one or more annotated radiograph images. After viewing the list of available X-rays for that patient, the clinician has selected a specific X-ray image 510, which has caused update of the user interface to display the selected image along with the various annotation content and condition information determined by the machine learning analysis. In the illustrated example, overlay bounding region 530 includes an overlaid textual label indicating the particular condition (in this instance "Root Canal"). In some embodiments, each displayed bounding region may include a displayed overlay text label indicating the name of the particular pathology, anatomy, restoration or anomaly that has been detected by the machine learning models. In other embodiments, labels may only be displayed as overlay content within the image for one or more particular pathologies or other conditions selected by the user from the lists 520 or 524 (such as the user's selection of the Root Canal condition option 524 in user interface 500).

In some embodiments, the clinician or other user selecting, clicking on, or rolling over a condition from lists 520 or 522 may cause that pathology or non-pathologic condition to be highlighted in an overlaid bounding box or other bounding region on the image, such as bounding boxes 530, 532 and 534. In some embodiments, each bounding region's shape within the overlay content may be color coded to indicate the confidence that the medical image analysis system 120 assigned to its identification of the particular pathology or condition label. For example, a green bounding box may indicate a high confidence score (falling above a first threshold), gold may indicate a medium confidence score (falling above a second threshold) and red may indicate a low confidence score (falling above a third threshold). In other embodiments different shapes, line styles or other visual differences may be used to distinguish confidence scores instead of or in addition to color differences.

The user may adjust confidence threshold control element 518 to either add or remove display of certain bounding regions and associated conditions based on their confidence score. At a very high setting, the confidence threshold may generally serve to minimize false alarms and maximize specificity and/or precision. At a very low setting, it may generally serve to minimize false negatives and maximize sensitivity and/or recall. Setting the confidence threshold control element to its absolute highest setting (such as a threshold of 100), may result in the user interface being updated to display no overlay metadata or bounding regions, such that the radiograph image is displayed without any overlay.

More specifically, a user adjusting the confidence threshold control element 518 (presented as a slider control) may change the bounding boxes displayed to display all bounding boxes associated with a pathology or other label having a machine learning confidence value at or above the threshold selected by the user via the control element 518 (set at a threshold of 40 out of 100 in the illustrated example). For example, if a user set the confidence threshold higher, such as to 80, a number of bounding boxes currently displayed and that have confidence thresholds between 40 and 79 may be removed from the displayed bounding region overlays on the given image.

As further shown in user interface 500, contrast control element 512 may enable the user to temporarily correct or adjust the display contrast of the image, such that aspects or anatomies appear brighter or better illuminated than in the original image. Overlays (including bounding region shapes and any associated text) may be preserved while contrast adjustment takes place. The zoom control 514 may enable the user to zoom in or out within the image, such as to inspect one or more specific regions of the image more closely. Overlays may also be preserved while zoom adjustment takes place. In other embodiments, a rotation tool (not illustrated) may additionally enable a user to rotate the displayed image, with the overlays also rotating and continuing to be displayed during image rotation. In some embodiments, the user interface may further display a recommended treatment plan for one or more pathologies, which may be determined from a stored association between a specific annotation label and a recommended treatment.

Additional Details Regarding Model Training and Testing

In some embodiments, the various machine learning models described herein may be trained using a large number of training and test images that have been annotated by highly respected dentists or other experts, such as using over one million annotated radiograph images in one embodiment. In some embodiments, training data may include X-ray images (stored as digital image files) that are each paired with metadata denoting pixel regions that contain the properties or features that a particular one or more of the machine learning models are configured to identify, such as a particular pathology.

The annotation data and/or other metadata may be generated based in part by experts marking or labeling regions in the training images via a user interface tool presented by the medical image analysis system 120 or an associated client-side application. A dentist or other expert using such an annotation tool at the training stage may view, via a user interface, an X-ray, a set of labels, and options for drawings rectangles or other bounding shapes over the X-ray in order for a label to be applied to that rectangle or bounding region (such as a label denoting a particular anatomy or pathology depicted or present within the pixel data included within the given bounding region). The user interface may instruct the user to, for example, "draw the smallest possible box that encloses the entire pathology." An annotator leveraging such an annotator tool may be presented with only a subset of all possible labels (such as those grouped within a single label category) in order to reduce errors by increasing the focus of the annotator on specific potential pathologies, anatomies or other features that one or more specific machine learning models will be trained to detect. Labels within a label category may be similar in morphology and/or root cause (for example, three different degrees of severity of caries), in some embodiments.

In some embodiments, the training image labeling process may include presenting two different dentists or other experts with the same images for labeling. Subsequent to two different users viewing the same radiograph and label category combination, the medical image analysis system may evaluate the annotations against each other with respect to relative positions (which may include evaluating overlap via a Jaccard index) and label. The Jaccard index, or intersection over union determination, is a measure of how much of the area of the bounding regions is the same compared to their combined area.

In one embodiment, the possible outcomes in comparing two annotations on the same radiograph from two different annotators are: (a) the two annotations agree in both position and label (in which case the system may consider this a verified annotation), (b) the two annotations agree in position, although the label is not the same but is from the same label category (which the system may mark as a confusion of severity), (c) the two annotations agree in label but not in position (which the system may mark as a confusion of size), or (d) an annotation from one annotator has no potential candidate for comparison in the other annotator's result (which the system may mark as a standard disagreement).

In some embodiments, certain particularly respected or accomplished dentists or other experts may be designated to resolve disagreements in other experts' annotations of the training images. A resolving expert may be presented a user interface that includes the subject radiograph with both sets of annotations (previously created by two experts other than the resolving expert) overlaid thereon. The user interface may enable the resolving expert to approve or deny a standard disagreement and select one, the other, or neither earlier annotation in the case of a confusion of severity or size. In some embodiments, the user interface may not allow the resolving expert to overrule a verified annotation of the two other experts. Once any disagreements are resolved for a given radiograph via interaction with one or more user interfaces, the final annotation bounding region location and size, as well as the associated label for each bounding region, may be stored as training data to be provided to one or more of the machine learning models.

Model Training and Evaluation

After a model has been trained using the above training data, the medical image analysis system 120 may evaluate the machine learning model's performance, which may be conducted on a per-model basis. A subset of the images that have been annotated and verified by experts (discussed above) may be used as a test set to gauge model performance. The test set contains images that the model was not exposed to in the training process. Performance may be measured, in some embodiments, based on each of precision, specificity, sensitivity (recall) and F1 score. These are defined as follows, according to one embodiment:

$$TP = \text{True Positive, } FP = \text{False Positive}$$

$$TN = \text{True Negative, } FN = \text{False Negative}$$

$$\text{Precision} = \frac{TP}{TP + FP}$$

-continued $$\text{Specificity} = \frac{TN}{TN + FP}$$

$$\text{Sensitivity} = \frac{TP}{TP + FN}$$

$$F1 \text{ score} = \frac{2 * \text{Precision} * \text{Sensitivity}}{\text{Precision} + \text{Sensitivity}}$$

Precision may be considered a measure of the likelihood that a prediction is true or false. Specificity may be considered a measure of the likelihood that a non-prediction does not contain an existing condition, anatomy, or other feature of interest. Sensitivity may be considered a measure of the likelihood an existing condition, anatomy, or other feature of interest is predicted. F1 score measures the overall performance of the model in view of both precision and sensitivity.

The determination of true positives, false positives, true negatives, and false negatives may be based at least in part on the spatial relationships between predicted region-property pairs and manually annotated region-property pairs. A predicted region may be either a true positive or a false positive. This may be delineated, for example, via thresholding the Jaccard index. For example, given two sets, A and B, the Jaccard index measures the intersection divided by the union of the regions. This quantifies the difference between the regions shared by A and B alongside the regions mutually exclusive to A and B. Given a specific Jaccard threshold, a prediction will be deemed a true or false positive by the system. During evaluation, the threshold may be varied and performance metrics calculated with respect to it. A region not predicted will either be a true negative or a false negative. The absence of a prediction may be deemed true or false via thresholding the Jaccard index.

Figure 6:
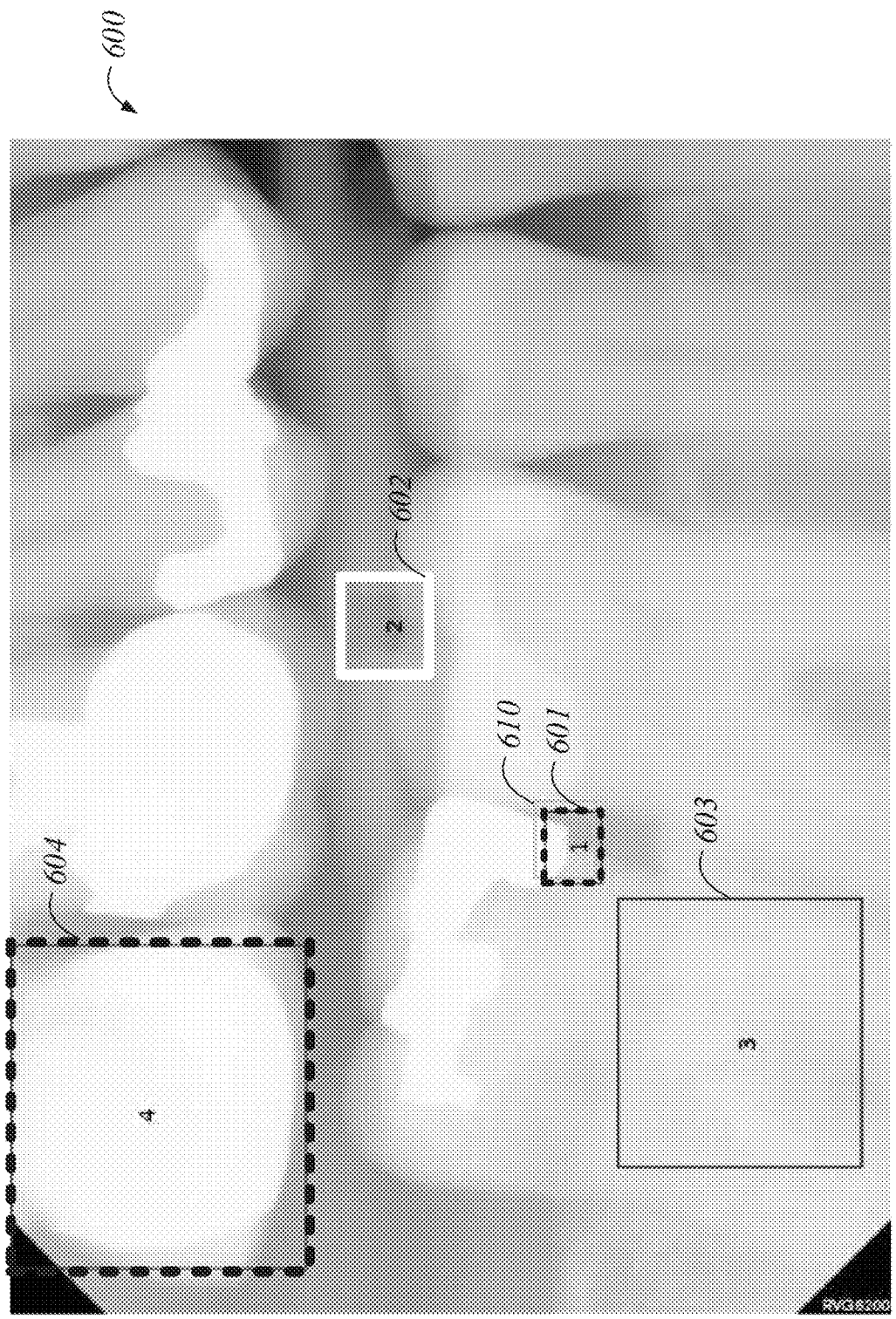
FIG. 6 depicts annotation regions that can be analyzed to determine machine learning model performance, such as by identifying each of a number of regions as a true positive, a false positive, a true negative or a false negative.

FIG. 6 depicts annotation regions that can be analyzed to determine machine learning model performance, such as by identifying each of a number of regions as a true positive, a false positive, a true negative or a false negative. In some embodiments, different colors may be displayed in a user interface for the bounding region shapes to visually signify the source of the bounding region (such as one color to denote an expert's annotation and a different color to denote an automated annotation by a machine learning model), but are instead depicted in FIG. 6 using different lines configurations (such as dashed versus solid black) for illustrative purposes only.

In the example image 600, which may be presented via a user interface, regions 601 and 604 have been annotated by experts. Annotation region 610 is a prediction from a machine learning model that the pixels within the region (e.g., pixels falling within the bounding rectangle 610) are classified as a certain Class 1 (such as caries of a certain severity). Annotation region 602 is a machine learning model annotation predicting Class 2. Region 603 is a region neither annotated by an export nor a machine model. In this example, using a Jaccard threshold of 85%, region 610 contains a true positive, region 602 contains a false positive, region 603 contains a true negative, and region 604 contains a false negative.

Figure 7:
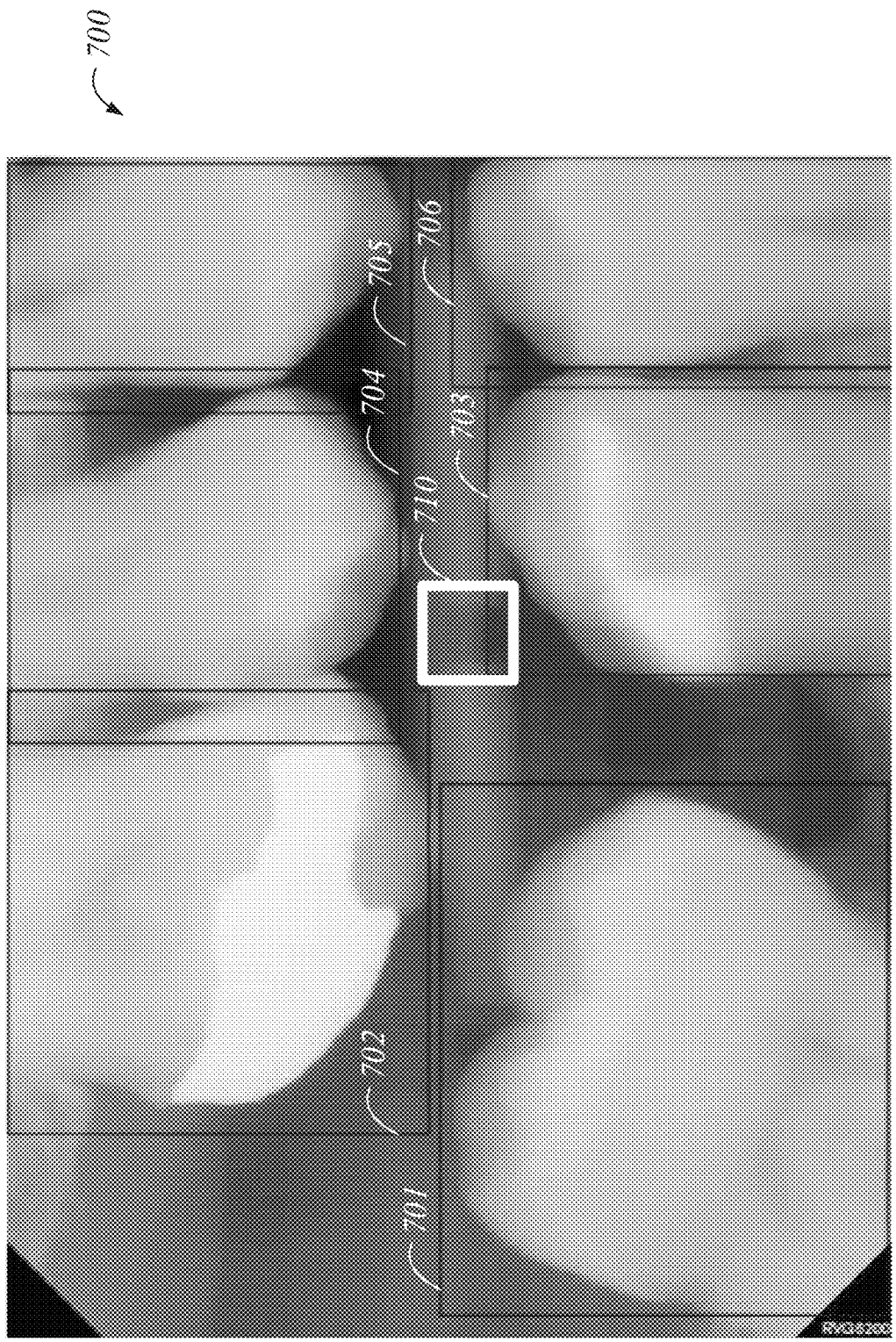
FIG. 7 depicts annotation regions corresponding to detected teeth and detected caries, which can be analyzed in a post-processing method to identify a false positive based on spatial relationship of the regions.

FIG. 7 depicts annotation regions corresponding to detected teeth and detected caries, which can be analyzed in a post-processing method to identify a false positive based on spatial relationship of the regions. It will be appreciated that other post-processing rules and analysis can be applied to other pathologies. In the illustrated example, teeth detected by one or more machine learning models have been marked by bounding regions 701-706. A separate machine learning model configured to detect caries has marked region 710. In the illustrated example, a post-processing module implemented by the medical image analysis system 120 may reject the caries classification marked by region 710 based on the spatial relationship of region 710 with detected anatomical regions (teeth) 701, 702, 703, 704, 705 and/or 706.

Post-processing may deem the classification of region 710 as caries to be a false positive due to a rule set or other logic indicating that caries cannot exist anywhere other than on a tooth. Thus, the given post-processing module may determine that the region 710 should not be marked or otherwise included in the annotation data to be returned to the API gateway 122, in some embodiments. More generally, various post-processing modules may be configured to reject machine learning models' classifications of given pathologies based on spatial relationships to other models' detected anatomical regions.

Figure 8:
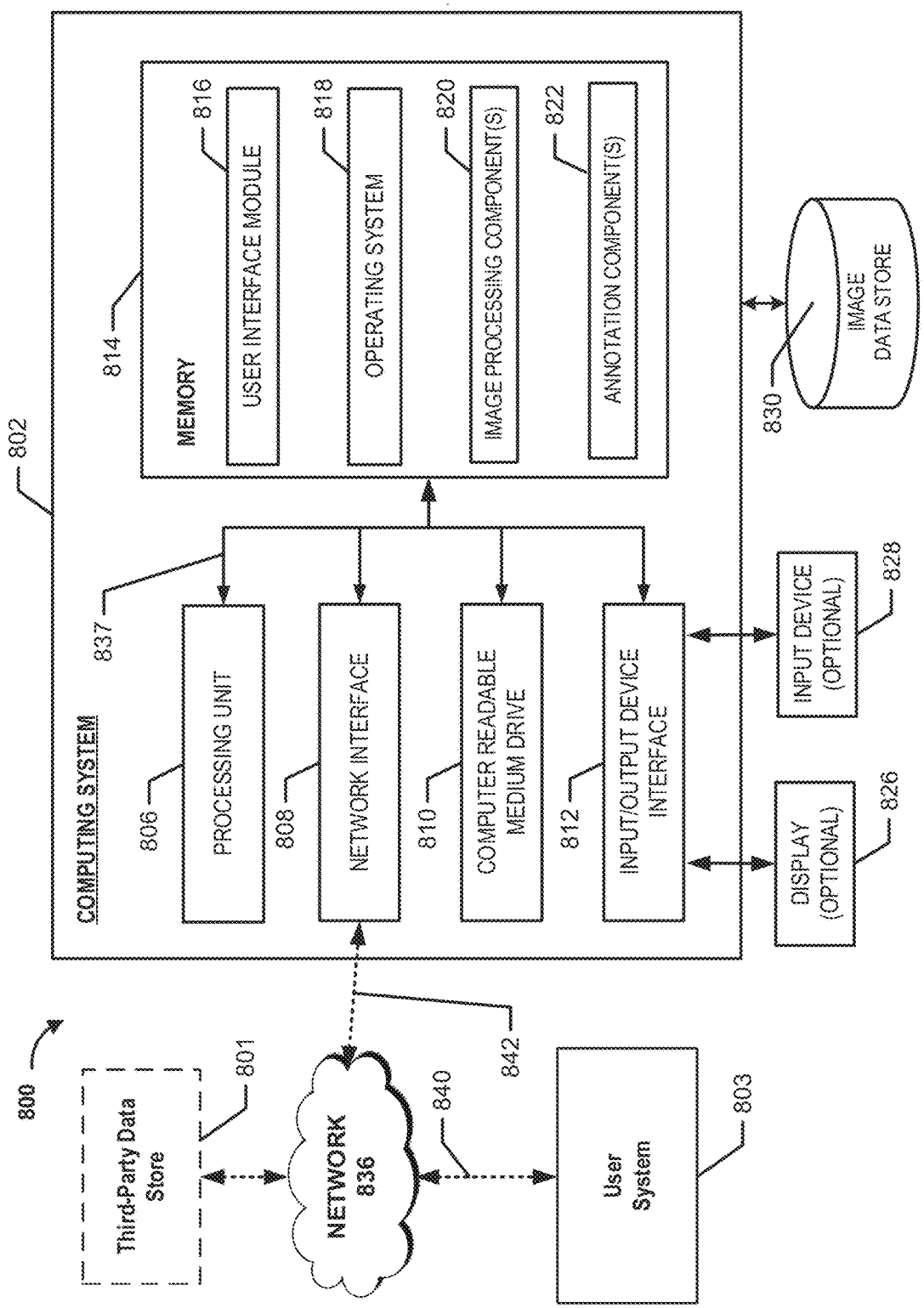
FIG. 8 is a system block diagram of a computing environment suitable for use in various embodiments of the present disclosure.

FIG. 8 illustrates a general architecture of a computing environment 800, according to some embodiments. As depicted in FIG. 8, the computing environment 800 may include a computing system 802. The general architecture of the computing system 802 may include an arrangement of computer hardware and software components used to implement aspects of the present disclosure. The computing system 802 may include many more (or fewer) elements than those shown in FIG. 8. It is not necessary, however, that all of these generally conventional elements be shown in order to provide an enabling disclosure. In some embodiments, the computing system 802 may be an example of what is referred to as the medical image analysis system above, though a medical provider system described above may include one or more similar components, in some embodiments.

As illustrated, the computing system 802 includes a processing unit 806, a network interface 808, a computer readable medium drive 810, an input/output device interface 812, an optional display 826, and an optional input device 828, all of which may communicate with one another by way of a communication bus 837. The processing unit 806 may communicate to and from memory 814 and may provide output information for the optional display 826 via the input/output device interface 812. The input/output device interface 812 may also accept input from the optional input device 828, such as a keyboard, mouse, digital pen, microphone, touch screen, gesture recognition system, voice recognition system, or other input device known in the art.

The memory 814 may contain computer program instructions (grouped as modules or components in some embodiments) that the processing unit 806 may execute in order to implement one or more embodiments described herein. The memory 814 may generally include RAM, ROM and/or other persistent, auxiliary or non-transitory computer-readable media. The memory 814 may store an operating system 818 that provides computer program instructions for use by the processing unit 806 in the general administration and operation of the computing system 802. The memory 814 may further include computer program instructions and other information for implementing aspects of the present disclosure. For example, in one embodiment, the memory 814 may include a user interface module 816 that generates user interfaces (and/or instructions therefor) for display upon a computing system, e.g., via a navigation interface such as a browser or application installed on the computing system 802 or the client computing system 803.

In some embodiments, the memory 814 may include one or more image processing components 820 and annotation components 822, which may be executed by the processing unit 806 to perform operations according to various embodiments described herein. The modules 820 and/or 822 may access the image data store 830 in order to retrieve and analyze image data and generate associated annotation data as described herein. The data store may be part of the computing system 802, remote from the computing system 802, and/or may be a network-based service.

In some embodiments, the network interface 808 may provide connectivity to one or more networks or computing systems, and the processing unit 806 may receive information and instructions from other computing systems or services via one or more networks. In the example illustrated in FIG. 8, the network interface 808 may be in communication with a client or user computing system 803 via the network 836, such as the Internet. In particular, the computing system 802 may establish a communication link 842 with a network 836 (e.g., using known protocols) in order to send communications to the computing system 803 over the network 836. Similarly, the computing system 803 may send communications to the computing system 802 over the network 836 via a wired or wireless communication link 840. In some embodiments, the computing system 802 may additionally communicate via the network 836 with an optional third-party data store or data service 801, which may be used by the computing system 802 to retrieve remotely stored image files.

Those skilled in the art will recognize that the computing systems 802 and 803 may be any of a number of computing systems including, but not limited to, a laptop, a personal computer, a mobile phone, a smartphone, a tablet computer, another wireless device, a set-top or other television box, one or more servers, and the like. The client computing system 803 may include similar hardware to that illustrated as being included in computing system 802, such as a display, processing unit, network interface, memory, operating system, etc. In some embodiments, the client computing system 803 may be a medical provider system as described above or may be utilized by a dentist marking images for machine learning training purposes or by dental lab personnel.

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

All of the processes described herein may be embodied in, and fully automated via, software code modules executed by a computing system that includes one or more general purpose computers or processors. The code modules may be stored in any type of non-transitory computer-readable medium or other computer storage device. Some or all the methods may alternatively be embodied in specialized computer hardware. In addition, the components referred to herein may be implemented in hardware, software, firmware or a combination thereof.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm elements described in connection with the embodiments disclosed herein can be implemented as electronic hardware, computer software, or combinations of both. To clearly illustrate this interchangeability of hardware and software, various illustrative components, blocks, modules, and elements have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a processing unit or processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

It should be emphasized that many variations and modifications may be made to the above-described embodiments, the elements of which are to be understood as being among other acceptable examples. All such modifications and variations are intended to be included herein within the scope of this disclosure.

What is claimed is:

1. A computer system comprising:
memory; and
a processor in communication with the memory and configured with processor-executable instructions to perform operations comprising:
training, using a plurality of training images depicting dental radiographs as training image data, a plurality of machine learning models to localize and classify dental pathologies, anatomies, restorations or anomalies present in the training image data, wherein at least a subset of the plurality of machine learning models comprise neural networks;
receiving, via an application programming interface (API), a request for image annotation data associated with a dental radiograph, wherein the request is received subsequent to the training of the plurality of machine learning models, and wherein the dental radiograph was not included in the plurality of training images;
obtaining a digital image file comprising the dental radiograph as image data;
initiating execution of two or more pre-processing modules, wherein a first pre-processing module is configured to modify the image data to generate pre-processed image data, wherein a second pre-processing module is configured to generate metadata associated with the image data;
initiating parallel execution of at least a subset of the plurality of machine learning models, wherein input features provided to individual machine learning models of the plurality of machine learning models are based at least in part on at least one of the pre-processed image data or the metadata;
obtaining results associated with output of each of the plurality machine learning models, wherein the results associated with an individual machine learning model comprise at least one of output of the individual machine learning model or output of a post-processing module coupled to the individual machine learning model; and
generating image annotation data based at least in part on the obtained results associated with output of the plurality of machine learning models, wherein the image annotation data indicates at least one location in the digital image file and an associated dental pathology, restoration, anatomy or anomaly detected at the at least one location by at least one of the plurality of machine learning models.

2. The computer system of claim 1, wherein at least one of the two or more pre-processing modules includes a machine learning model.

3. The computer system of claim 1, wherein the request for the image annotation data is received over a network from a computing system operated by a dental practice.

4. The computer system of claim 1, wherein individual machine learning models of at least a subset of the plurality of machine learning models are each coupled to a different post-processing module.

5. The computer system of claim 1, wherein at least one input feature to a first model of the plurality of machine learning models is generated by a second model of the plurality of machine learning models.

6. The computer system of claim 1, wherein a subset of the plurality of machine learning models comprise ensemble detectors that are collectively configured to predict presence of a plurality of dental pathologies in an image.

7. The computer system of claim 1, wherein a first model of the plurality of machine learning models is trained to detect a same pathology as a second model of the plurality of machine learning models using a different machine learning algorithm than the second model.

8. The computer system of claim 1, wherein the operations further comprise, prior to including in the image annotation data a first pathology predicted at a first location in the digital image file by a first machine learning model, confirming that a second machine learning model classified a portion of the image data at or near the location as depicting a first anatomy associated with the first pathology.

9. The computer system of claim 8, wherein the first pathology is caries, wherein the first anatomy is a tooth.

10. The computer system of claim 1, wherein a first machine learning model of the plurality of machine learning models is trained to detect each of at least ten different dental pathology classifications.

11. The computer system of claim 1, wherein the dental pathology, restoration, anatomy or anomaly detected at the at least one location is one of caries, bone loss, an existing dental restoration, or tooth decay.

12. A computer-implemented method comprising:

training, using a plurality of training images depicting dental radiographs as training image data, a plurality of machine learning models to localize and classify dental pathologies, anatomies, restorations or anomalies present in the training image data, wherein at least a subset of the plurality of machine learning models comprise neural networks;

obtaining a digital image file comprising a dental radiograph as image data, wherein the digital image file was not included in the plurality of training images;

performing a plurality of pre-processing operations with respect to the image data, wherein the plurality of pre-processing operations comprise at least one of (a) modifying the image data to generate pre-processed image data, or (b) generating metadata associated with the image data;

providing input features associated with the image data to at least the plurality of machine learning models, wherein the input features provided to individual machine learning models of the plurality of machine learning models are based at least in part on at least one of the pre-processed image data or the metadata associated with the image data;

obtaining results associated with output of each of the plurality machine learning models, wherein the results associated with an individual machine learning model comprise at least one of output of the individual machine learning model or output of a post-processing module coupled to the individual machine learning model; and generating image annotation data based at least in part on the obtained results associated with output of the plurality of machine learning models, wherein the image annotation data indicates at least one location in the digital image file and an associated dental pathology, restoration, anatomy or anomaly detected at the at least one location by at least one of the plurality of machine learning models.

13. The computer-implemented method of claim 12 further comprising transmitting the image annotation data to a computing system that sent a request for the image annotation data, wherein the image annotation data is formatted to cause an application operated on the computing system to visually indicate presence of one or more dental pathologies by displaying one or more visual bounding shapes overlaid on one or more regions of the dental radiograph within a user interface.

14. The computer-implemented method of claim 12, wherein the least one location identified in the image annotation data is associated with a bounding shape having a size defined in the image annotation data.

15. The computer-implemented method of claim 14, wherein image annotation data includes, for a first pathology: a pathology name label, at least one pair of x and y coordinates associated with a first bounding shape determined for the first pathology, and dimension information defining a size of the first bounding shape.

16. The computer-implemented method of claim 12 further comprising determining a confidence score associated with each dental pathology, restoration, anatomy or anomaly identified in the image data by the plurality of machine learning models, wherein the image annotation data includes a first determined confidence score associated with the at least one location in the digital image file.

17. The computer-implemented method of claim 12 further comprising, prior to including in the image annotation data a first pathology predicted at a first location in the digital image file by a first machine learning model, confirming that a second machine learning model classified a portion of the image data at or near the location as depicting a first anatomy associated with the first pathology.

18. A non-transitory computer readable medium storing computer executable instructions that, when executed by one or more computer systems, configure the one or more computer systems to perform operations comprising:

training, using a plurality of training images comprising dental radiographs as training image data, a plurality of machine learning models to localize and classify dental pathologies depicted in the training image data, wherein at least a subset of the plurality of machine learning models comprise neural networks;

obtaining a digital image file comprising a dental radiograph as image data, wherein the digital image file was not included in the plurality of training images;

performing a plurality of pre-processing operations with respect to the image data, wherein the plurality of pre-processing operations comprise at least one of (a) modifying the image data to generate pre-processed image data, or (b) generating metadata associated with the image data;

providing input features associated with the image data to two or more of the plurality of machine learning models, wherein the input features provided to individual machine learning models of the plurality of machine learning models are based at least in part on at least one of the pre-processed image data or the metadata associated with the image data;

obtaining results associated with output of each of the plurality machine learning models, wherein the results associated with an individual machine learning model comprise at least one of output of the individual machine learning model or output of a post-processing module coupled to the individual machine learning model; and generating image annotation data based at least in part on the obtained results associated with output of the plurality of machine learning models, wherein the image annotation data indicates at least one location in the digital image file and an associated dental pathology detected at the at least one location by at least one of the plurality of machine learning models.

19. The non-transitory computer readable medium of claim 18, wherein the plurality of machine learning models include at least two different types of convolutional neural networks that are each trained to identify a different dental pathology.

20. The non-transitory computer readable medium of claim 18, wherein at least one input feature to a first model of the plurality of machine learning models is generated by a second model of the plurality of machine learning models.

* * * * *